(12) United States Patent
Edvardsson et al.

(10) Patent No.: US 7,981,355 B2
(45) Date of Patent: Jul. 19, 2011

(54) MAT-FORMING WHEEL

(75) Inventors: Gunnar Edvardsson, Bohus Björkö (SE); Mårten Alkhagen, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 228 days.

(21) Appl. No.: 12/373,728

(22) PCT Filed: Jul. 20, 2006

(86) PCT No.: PCT/SE2006/050268
§ 371 (c)(1),
(2), (4) Date: Jan. 14, 2009

(87) PCT Pub. No.: WO2008/010753
PCT Pub. Date: Jan. 24, 2008

(65) Prior Publication Data
US 2010/0013118 A1    Jan. 21, 2010

(51) Int. Cl.
*B27N 3/08* (2006.01)
(52) U.S. Cl. ........ 264/517; 264/299; 264/310; 264/319; 425/436 R
(58) Field of Classification Search .......................... None
See application file for complete search history.

(56) References Cited

U.S. PATENT DOCUMENTS

| | | |
|---|---|---|
| 3,973,291 A | 8/1976 | Kolbach |
| 4,388,056 A | 6/1983 | Lee et al. |
| 4,598,441 A | 7/1986 | Stemmler |
| 5,030,314 A | 7/1991 | Lang |
| 5,575,874 A | 11/1996 | Griesbach, III et al. |
| 6,330,735 B1 | 12/2001 | Hahn et al. |
| 6,652,798 B1 | 11/2003 | Edvardsson |
| 6,811,642 B2 | 11/2004 | Ochi |
| 2002/0056516 A1 | 5/2002 | Ochi |
| 2005/0109442 A1 | 5/2005 | Neubauer et al. |
| 2006/0021695 A1 | 2/2006 | Blessing et al. |
| 2006/0024433 A1 | 2/2006 | Blessing et al. |
| 2006/0048880 A1 | 3/2006 | Blessing et al. |

FOREIGN PATENT DOCUMENTS

| | | |
|---|---|---|
| DE | 1 510 427 B | 10/1970 |
| DE | 43 35 919 A1 | 4/1995 |
| EP | 0 292 624 A1 | 11/1988 |
| EP | 0 958 801 A1 | 11/1999 |
| EP | 1 082 081 B1 | 3/2001 |
| EP | 0 958 801 B1 | 9/2004 |
| EP | 1 621 167 A1 | 2/2006 |
| FR | 2 690 843 A1 | 11/1993 |

(Continued)

OTHER PUBLICATIONS

* Form PCT/ISA/210 (International Search Report) dated Mar. 5, 2007.

(Continued)

*Primary Examiner* — Monica A Huson
(74) *Attorney, Agent, or Firm* — Buchanan Ingersoll & Rooney PC

(57) ABSTRACT

A mat-forming wheel for forming air-laid absorbent cores for sanitary absorbent articles, such as diapers, sanitary napkins, incontinence protectors and the like, said wheel having a series of moulds along its peripheral surface, each mould having up-standing walls and a bottom. The up-standing walls of the mould are formed in an element of a flexible material, which element is releasably attached to a foraminous substrate of rigid material, which runs along the whole circumference of the mat-forming wheel.

12 Claims, 2 Drawing Sheets

FOREIGN PATENT DOCUMENTS

| | | |
|---|---|---|
| RU | 2227001 | 4/2004 |
| WO | WO 99/60964 A1 | 12/1999 |
| WO | WO 2005/072671 A1 | 8/2005 |

OTHER PUBLICATIONS

* Form PCT/ISA/237 (Written Opinion of the International Searching Authority) dated Mar. 5, 2007.
* Form PCT/IPEA/409 (International Preliminary Report on Patentability) dated Sep. 19, 2008.

U.S. Appl. No. 12/373,780, Edvardsson, "An Apparatus and Method for Forming Air-Laid Absorbent Cores", filed Jan. 14, 2009.

U.S. Appl. No. 12/373,786, Edvardsson et al., "An Apparatus and Method for Forming Air-Laid Absorbent Cores", filed Jan. 14, 2009.

U.S. Appl. No. 12/373,729, Gunnar Edvardsson, "An Apparatus and Method for Forming Air-Laid Absorbent Cores", filed Jan. 14, 2009.

Decision of Grant issued in the corresponding Russian Patent Application, Application No. 2009105882, issued Jul. 13, 2010 and English translation thereof.

MAT-FORMING WHEEL

TECHNICAL FIELD

The present disclosure relates to a mat-forming wheel for forming air-laid absorbent cores for sanitary absorbent articles, such as diapers, sanitary napkins, incontinence protectors and the like, said wheel comprising a series of moulds along its peripheral surface, each mould comprising up-standing walls and a bottom. The disclosure also relates to a method of forming absorbent articles made possible by the use of such mat-forming wheels

BACKGROUND

Mat-forming wheels are components that often are present in lines for the manufacturing of disposable, sanitary absorbent articles, such as diapers, sanitary napkins, incontinence protectors and the like. Sometimes such articles are manufactured in rather small batches. Those batches can consist of different types of articles or different sizes of the same article. When different batches are to be produced after each other in the same manufacturing line, which is often the case, this involves a change of moulds on the mat-forming wheel. The moulds can for example consist of mould plates of solid stainless steel and the exchange of all these plates for different mould plates is time-consuming, which is a problem, especially if a series of small batches are to be produced. There is therefore a need for a mould construction which is easy to mount and remove for shortening the time of stand-still for the mat-forming wheel and thereby the whole manufacturing line. It is of course important to shorten the time of stand-still also when different large batches shall be manufactured.

Nowadays, discrete particles of highly absorbent material, so called superabsorbent material (SAP), are often mixed in the fibres to be deposited in the moulds of a mat-forming wheel. The mixture of fibres and SAP-particles are drawn into the moulds by suction forces created by suction boxes located in the interior of the mat-forming wheel, and the mixture of fibres and SAP-particles has a considerable speed when entering the mould openings. There is therefore a great risk that the SAP-particles will bounce out of a mould when encountering a wall of the mould. This is a problem both with respect of cost and contamination of the environment or contamination of other components in the manufacturing line. Another problem caused by SAP-particles is that they wear out moulds and thereby makes it necessary to change moulds without changing the articles manufactured. Also for this reason, a mould that is easy to mount and remove is desirable.

U.S. Pat. No. 3,973,291 discloses an endless open mesh container to which a relatively thick substrate, which can be made of natural rubber or a foam material, is adhered by glue or adhesive. There is no mention in this document that the substrate shall be releasbly attached to the endless container.

OBJECTS AND SUMMARY

The objective of the present disclosure is to satisfy the need for easily interchangeable moulds on a mat-forming wheel and at the same time reduce the problem of SAP-particles bouncing out of such moulds. A further objective is reduce the risk for SAP-particles falling out of core elements during transfer.

The objectives of the present disclosure are obtained by a mat-forming wheel for forming air-laid absorbent cores for sanitary absorbent articles, such as diapers, sanitary napkins, incontinence protectors and the like, said wheel comprising a series of moulds along its peripheral surface, each mould comprising up-standing walls and a bottom, characterised in that the upstanding walls of the mould is formed in an element of a flexible material, which element is releasably attached to a foraminous substrate of rigid material, which runs along the whole circumference of the mat-forming wheel, wherein the up-standing walls of the moulds are walls in through-going openings in said element, which element contains a row of such mould openings, and wherein said element is made of a soft material.

In a first alternative, the mat-forming wheel includes one said element extending around the whole circumference of the mat-forming wheel.

In a second alternative, the mat-forming wheel includes several said elements, each extending over a portion of circumference of the mat-forming wheel.

Said element or elements are made of a soft material, preferably rubber, especially cellular, neoprene rubber.

Said element or elements can contain three layers, two layers of soft material and a layer of a stiffening material intermediate these two layers.

The foraminous substrate is a perforated steel plate or a band of wire mesh.

The disclosure also relates to a method of forming air-laid absorbent cores, comprising the steps of; forming first and second core elements by air-laying of air-entrained fibrous material to moulds on a first and second mat-forming wheel, each of said mat-forming wheels having a series of moulds according to the disclosure along their peripheral surface, transferring a core element on the second mat-forming wheel onto a core element on the first mat-forming wheel while the latter core element still is maintained in its mould by suction means, characterized by forming such a nip between the two mat-forming wheels that the distance between the peripheries of said wheels is less than 2 mm. By having such a small distance between the wheels, the risk for SAP-particles to fall out of the core elements during transfer is greatly reduced. However, due to the usual small ovality of the mat-forming wheels such a small nominal distance between the wheels will usually lead to that some of the moulds actually will be inside the periphery of the opposite wheel. This means that the method stated above can only be used with moulds of a resilient material allowing compression thereof.

In a preferred embodiment the nip is formed so that the distance between the peripheries of first and second mat-forming wheels is negative so that the moulds of the first and second mat-forming wheels will compress each other in the nip. By such an embodiment the risk for SAP-particles to fall out of a core element during transfer is even more reduced.

BRIEF DESCRIPTION OF THE DRAWINGS

The disclosure shall now be described with reference to the enclosed Figures, which are for the purpose of illustration of various non-limiting embodiments of the disclosure, of which, FIG. 1 schematically shows an apparatus for forming absorbent cores having mat-forming wheels according to a preferred embodiment of the present disclosure, FIG. 2 schematically shows part of a mat-forming wheel in the apparatus in FIG. 1.

DESCRIPTION OF EMBODIMENTS

Figure 1:
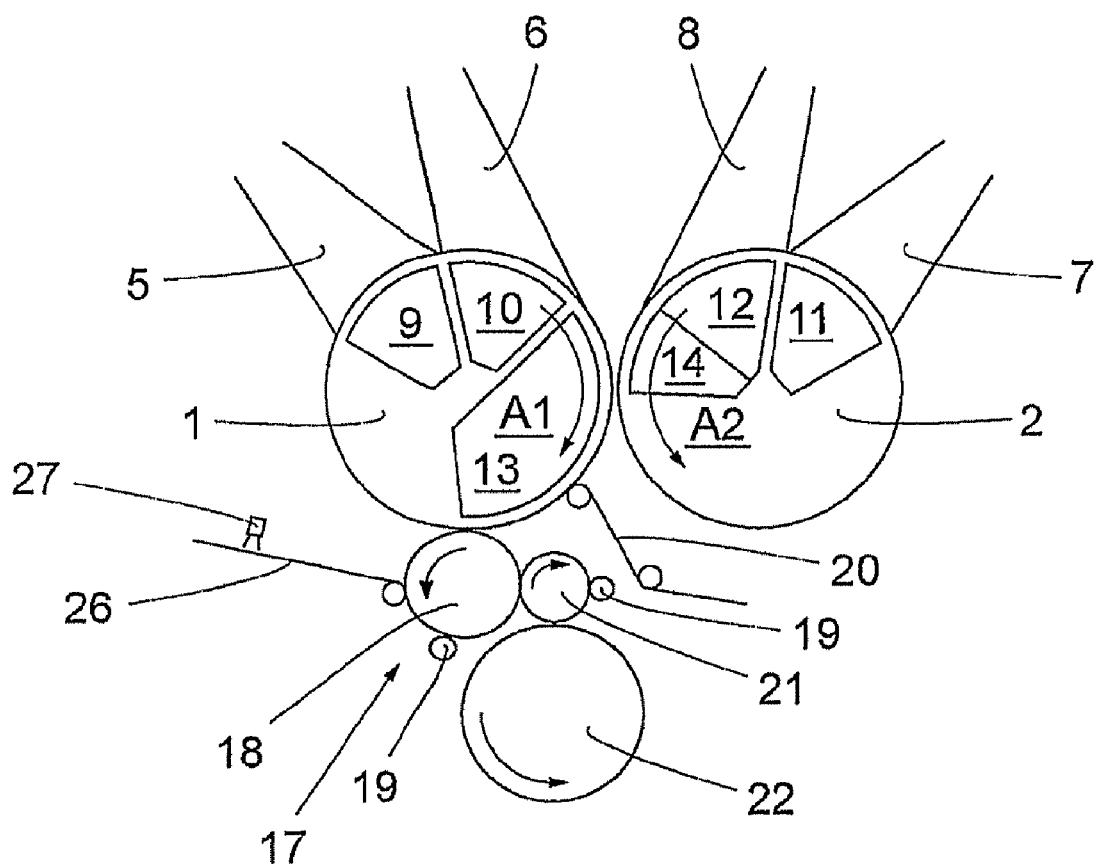

FIG. 1 discloses schematically an apparatus in which mat-forming wheels according to the present disclosure is used to advantage. The apparatus includes two formation drums or mat-forming wheels, a first wheel 1 and a second wheel 2, each having a series of moulds on their peripheral surfaces. The mould bottom or screen 29 (see FIG. 2) can be made of wire mesh or perforated steel sheet. Associated to the peripheral surfaces of the two mat-forming wheels 1,2 are two formation chambers or hoods 5,6 and 7,8, respectively, for each wheel. The apparatus also comprises a mill, for example a hammer mill, for defibrating of pulp, pipes used for fibre or fibre/SAP transport, and a fan for the transport of fibre or fibre/SAP to the respective hood 5-8. These components are conventional and well know to one skilled in the art. Each hood 5-8 is associated with a separate suction box 9,10 and 11,12, respectively, which is stationary and located in the interior of the respective mat-forming wheel, i.e. suction boxes 9,10 are disposed inside the first wheel 1 and suction boxes 11,12 are disposed inside the second wheel 2. When the moulds on the peripheral surface of each wheel pass between a hood and its associated suction box during the rotation of the wheel, the air-entrained material in the hood will be drawn into the mould and deposited therein. In the mat-forming wheels 1,2, suction boxes 13 and 14, respectively, are present for maintaining the core elements formed in the moulds in the their respective mould and for maintaining the shape of the formed core elements.

The mat-forming wheels 1,2 are disposed side-by-side and a nip is formed between them. The term "nip" denotes the point at which the peripheries of the wheels 1,2 are closest to each other.

In the apparatus according to FIG. 1, the second core element formed on the second mat-forming wheel 2 is transferred onto the first core element formed on the first mat-forming wheel 1 and held thereon by the suction created by suction box 13 until the composite core comprising first and second core elements is delivered to a compression device 17 consisting of two rollers 18,19. Near the nip between the wheels 1 and 2 and between the nip and the compression device 17, a web 20 of casing material, for example tissue, from a supply roll (not shown) is applied to the outer side of the composite core.

After compression, the composite core passes through a cutting device 21 and is then transferred to an accelerator device 22 before it is delivered into the line for manufacturing of absorbent articles of which the apparatus according to the disclosure is a part.

The apparatus illustrated in FIG. 1 is used in the following way.

As the mat-forming wheels 1,2 rotates in the direction of arrows A1 and A2, the moulds on the respective wheel first passes between the hood 5 respective 7 and the suction box 9 respective 11. During this passage a thin layer of pure pulp fibres is air-laid in the moulds. Thereafter the moulds on the respective matforming wheel pass between the hood 6 respective 8 and suction box 10 respective 12. During this passage a layer of a mixture of pulp fibres and SAP-particles is air-laid in the moulds covering the layer of pure pulp fibres. The concentration of SAP-particles (50-70%) in this layer in moulds of the second mat-forming wheel is much higher than in the moulds on the first mat-forming wheel. The layers of pure pulp fibres have the functions of preventing SAP-particles from obstructing and clogging the holes in the mould bottom, thereby causing an uneven distribution of air resulting in an uneven distribution of air-laid material, and from damaging the these bottom. It has surprisingly been shown that SAP-particles in a mixture of pulp fibres and SAP-particles can wear out the material in the mould bottoms. The layers also have the function of preventing SAP-particles from falling out of the core element formed in the respective mould during transport of the moulds on the respective wheel, during transfer of the second core element onto the first core element and during transfer of the composite core from wheel 1 to the compression device.

The moulds on the wheel 1,2 are shallower than the core elements formed therein. After the core elements have been formed by air-laying of layers in the respective moulds, the core elements are maintained in their respective mould by suction boxes 13 respective 14 until they reach the nip between the mat-forming wheels 1,2.

The nip is dimensioned so that the outsides of the core elements, i.e. the sides thereof distal from the respective mould bottom, abut each other in the nip. In other words, the nip constitutes a "marrying point" for the two core elements in which they get together. The nip is preferably dimensioned so that normally the core elements are slightly compressed in the marrying point. The suction box 14 in the second mat-forming wheel 2 ends at the marrying point. When the leading edge of the core element during the continued rotation of wheels 1,2 leaves the marrying point it will now longer be subjected to suction forces maintaining it on wheel 2 but only the suction forces of suction box 13 on wheel 1. These suction forces will maintain the leading edge of the second core element in abutment with the leading edge of a first core element in a mould of wheel 1. Due to the arrangement of the nip and the "overfilling" of moulds, all points of a second core element will in the nip come to abutment with the outside of a first core element while it still is maintained in mould and is not until then transferred onto a first core element. Thus an extremely controlled and accurate transfer of core elements is accomplished. The core element is thus subjected to suction forces from either suction box 14 on wheel 2 or suction box 13 during the whole transfer. No part of the core element is thus left in free air during transfer. Losses of SAP-particles out of core element is thereby significantly reduced in relation to a transfer operation in which the core element or portions thereof are moving in free air when centrifugal and gravitation forces are not counteracted by suction forces.

After the second core element has been transferred to wheel 1 onto the first core element, the thin protective layer of the second core element will prevent SAP-particles from falling out of this core element.

A web 20 of casing material, e.g. tissue, is applied to the composite core transported on the wheel 1 after passing of the nip. A further web 26 of casing material is applied to the side of core opposite to the side to which web 20 is applied after the core have left wheel 1 but before it passes between the rollers 18,19 of the compression device. Preferably, an adhesive coating is applied to web 26 by a glue applicator 27 before it is applied to the composite core 15,16.

Figure 2:
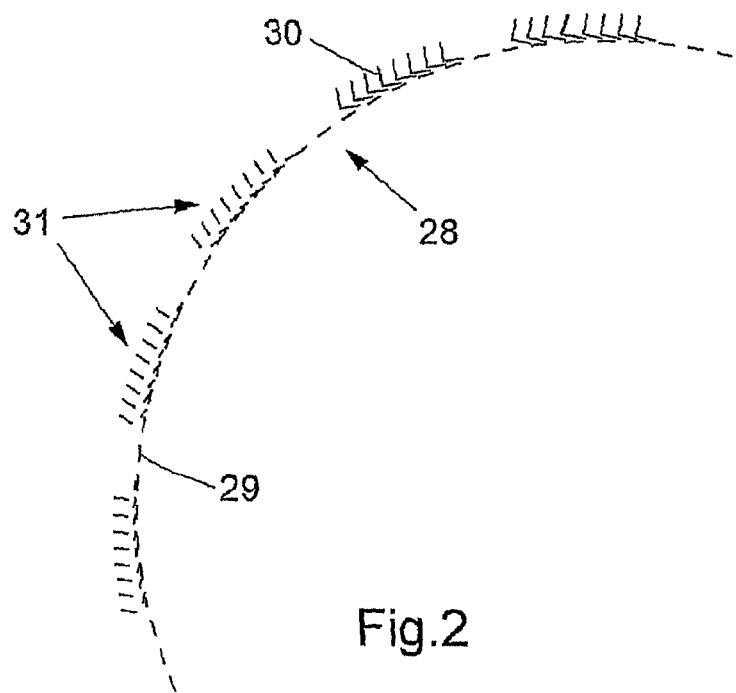

In FIG. 2, a part of the peripheral surface 28 of the mat-forming wheel 2 is shown in cross-section. This surface 28 is constituted by a steel plate 29 which is permanently affixed to the mat-forming wheel 2 and reaches around the circumference thereof. The steel plate 29 is perforated over its whole surface. Outside of the steel plate 29, an element 30 is releasably attached to the mat-forming wheel. This element has a row of through-going mould openings 31 along its length, i.e. the row is extended in the circumferential direction of the wheel 2. The mould openings 31 have a form corresponding to the contour of the second core elements formed on mat-forming wheel 2. The element 30 should cover all perforations in the steel plate 29 except the perforations located in the mould openings 31. For this reason the element 30 should preferably be made of an air-impermeable material or contain an air-impermeable layer and it should be attached to the mat-forming wheel so that it can seal the above mentioned perforations in the steel plate 29. However, as long as the air-permeability of element 30 is much less than the air-permeability of the steel plate, the air-borne fibres and possible SAP-particles will gather in the mould openings so the element 30 need not be totally air-impermeable even if this is preferred.

Figure 3:
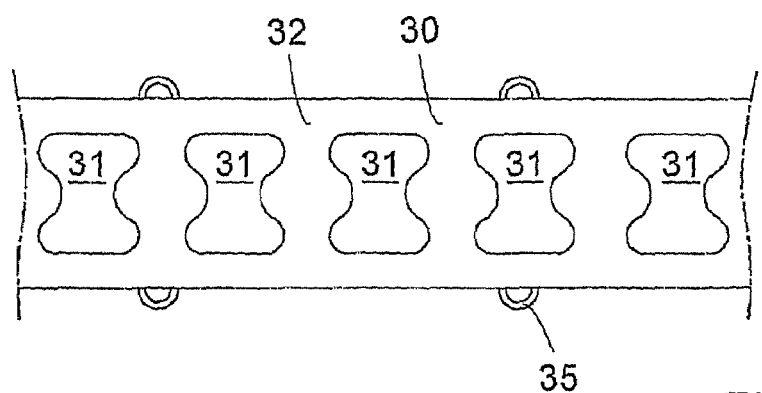
FIGS. 3 and 4 shows a plan view and a sectional view, respectively, of an element constituting a component of a mat-forming wheel in the apparatus of FIG. 1.
Figure 4:
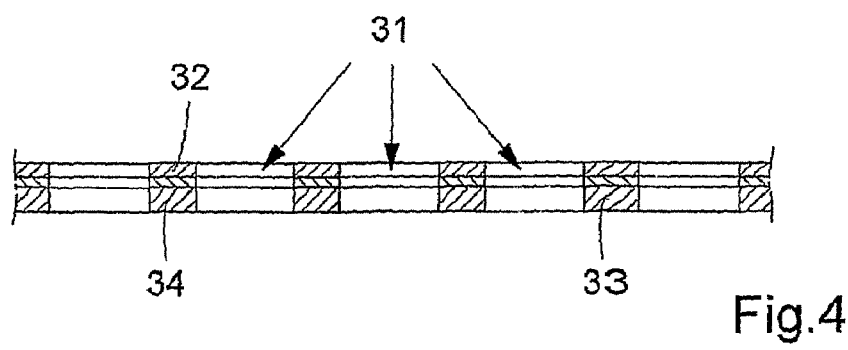

In FIGS. 3 and 4 a plan view and a cross-sectional view of element 30 is shown. In the embodiment shown element 30 is multi-layered and is composed of an upper layer 32 and a lower layer 33 of soft material and an intermediate stiffening layer 34. The layers 32,33 of soft material can be rubber material. The soft materials 32,33 can be the same or different. The intermediate layer 34 is preferably a thin metal sheet, for example made of stainless steel and the three layers are bonded to each other.

Preferred materials for the soft layer or soft layers of element 30 are closed or open celled rubber, for example cellular neoprene rubber. Other examples of suitable materials are polyurethane foam, silicon based foam materials, silicon based rubber.

The element 30 should also have means for releasable attachment to the mat-forming wheel 2. These means can consist of easily releasable mechanical attachments, such as toggle joint mechanisms comprising spring elements for resiliently holding element 30 against the steel plate 29, bayonet locks, hooks and straps or the like simple couplings. In FIG. 3, eyes 35 integral with the intermediate stiffening layer 34 and protruding from the sides of element 30 are shown, into which eyes bayonet screws can be inserted and screwed into co-operating holes in the mat-forming wheel. The eyes 35 can also be used for the insertion of hooks or the like affixed to the mat-forming wheel by toggle joint mechanisms or the like. It is also possible to make loops of resilient material from one of the layers of soft material protruding form the sides of element 30 the same way as elements 35 and attach such elements to fixed hooks members on the mat-forming wheel. It is also possible to make attachment holes in element 30 and insert the male member of a bayonet lock or a simple screw in such holes but it is preferred to use couplings which have no parts standing up from the outer surface of element 30.

In FIG. 3, the mould openings 31 have the form of core elements with their sides turned against each other. It is of course possible to design these openings so that the ends of the formed core elements are turned against each other.

It is also possible to attach element 30 to steel plate 29 by a releasable adhesive, i.e. an adhesive bond allowing the element 30 to be released intact and without deformation from steel plate 29, preferably a hot melt adhesive.

Element 30 is preferably extending over a large part of the circumference of the mat-wheel, for example over half the circumference thereof. It is of course also possible to let element 30 be extended over the whole circumference but such a long element might be more difficult to handle. In order to be easily releasable in the sense of the present disclosure, the element 30 shall contain a row of moulds and thereby extend over at least a quarter of the circumference of the mat-forming wheel.

As evident from the description of the apparatus of FIG. 1, the absorbent core elements formed in the moulds can be used in an apparatus in which the formed core elements is superposed on each other in the nip between two mat-forming wheels and that the formed core elements shall abut each other immediately before the transfer. This can be a problem when very thin core elements shall be superposed on each other since the mat-forming wheels often do not have perfectly circular cross-sections but a slight ovality. If the manufacturing tolerance of the mat-forming wheels is for example 2 mm the nip between the mat-forming wheels should be at least 4 mm. This distance can however be reduced when the elements 30 are made of a soft resilient material which can deform if the ovality of the mat-forming wheels makes portions of elements 30 press against each in the nip. The soft material in the elements 30 thus allows very thin core elements to be formed and increases also the accuracy of the whole forming process of thin core elements. This ability of elements 30 to be compressed can be used to advantage in the method described with reference to FIG. 1 by forming the nip between the mat-forming wheels 1,2 that the distance between the peripheries of said wheels is less than 2 mm. Such a small distance will lead to that some of the moulds will be compressed by each other in the nip due to the slight ovality of the wheels. By the fact that the elements 30 can be compressed by each other, the mat-forming wheels can be located with a nominal distance between them being less than the double tolerance value of ovality given by the manufacturer. The less the distance is between the moulds on the respective mat-forming wheel in the nip, the less risk for losses of SAP-particles. The risk for SAP-particles to bounce out of their moulds or fall out of their core elements during transfer is thus greatly reduced by the step of placing the moulds near each other in the nip.

It is even possible to have a negative nominal distance between the moulds in the nip between the mat-forming wheels in order to ensure that all moulds will be pressed together in the nip in order to virtually eliminate the risk for SAP-particles to fall out of the core elements during transfer.

By "nominal" distance is meant the distance in the nip between totally circular peripheries of the mat-forming wheels.

The soft material in the walls of mould openings also have good damping properties and thereby slows down SAP-particles encountering these walls during air-laying which reduces the amount of SAP-particles bouncing out of a mould during air-laying.

In the apparatus described with reference to FIG. 1, a large part of the core elements are formed by "over-filling" of the moulds, i.e. the core elements are shaped and the formed shapes are maintained by suction forces. Thus, a large part of the formed core elements are located outside of the moulds, only a smaller part of the air-laid mixture of fibres and SAP-particles being deposited within the interior of the moulds. This means firstly that it is essential that the elements 30 are sealingly covering the perforations in the steel plate 29 outside the mould openings and secondly that the elements 30 can be very thin without adversely affect the forming of the core elements as long as they are air-impermeable and can be sealingly attached to the steel plate 29. The element 30 can thus consist of a thin band of material being provided with a coating of a releasable adhesive, for example a pressure sensitive adhesive, such as hot melt pressure sensitive adhesive, Such elements 30 can be wounded up on storage rollers, like a tape. This allows a very easy way of attaching element 30 to the mat-forming wheel by placing the leading edge of the element in the right place on the mat-forming wheel and then unwound element 30 from the storage roller by rotating the mat-forming wheel. When such an element should be changed, the leading edge thereof is attached to the storage roller and unwound from the mat-forming wheel during the wounding onto the storage roller. Such elements 30 are preferably extending the whole circumference of the mat-forming wheel.

The described embodiments can of course be modified without leaving the scope of disclosure. For example, can the mould openings have other shapes than the shown hour-glass shape. The mat-forming wheels can be used in other apparatuses in manufacturing lines for absorbent articles than the apparatus according to FIG. 1. Other materials can be used for elements 30 or substrate 29 and element 30 can have less or more layers than described, for example can element 30 in FIGS. 2 and 3 consist of only one layer. Only one of the mat-forming wheels can have elements 30 according to the disclosure. The scope of disclosure should therefore only be limited by the content of the granted patent claims.

The invention claimed is:

1. A method of forming air-laid absorbent cores, comprising the steps of:
    forming first and second core elements by air-laying of air-entrained fibrous material to moulds on a first and second mat-forming wheel, at least one of said mat-forming wheels having a series of moulds along its peripheral surface, wherein said wheel comprises: (a) a foraminous substrate of rigid material, (b) an element of a flexible material, which element is releasably attached to the foraminous substrate, which runs along the whole circumference of the mat-forming wheel, and (c) a row of through-going mould openings in said flexible material, wherein the mould openings include up-standing walls,
    transferring a core element on the second mat-forming wheel onto a core element on the first mat-forming wheel while the latter core element still is maintained in its mould by suction means,
    wherein the method further comprises:
    forming a nip between the two mat-forming wheels such that the distance between the peripheries of said wheels is less than 2 mm.

2. The method according to claim 1, wherein the nip is formed so that the distance between the peripheries of first and second mat-forming wheels is negative so that moulds of the first and second mat-forming wheels will compress each other in the nip.

3. The method according to claim 1, wherein the soft material is a resilient material allowing compression thereof.

4. A mat-forming wheel for forming air-laid absorbent cores for sanitary absorbent articles, said wheel comprising a series of moulds along its peripheral surface, wherein said wheel comprises: (a) a foraminous substrate of rigid material, (b) an element of a flexible material, which element is releasably attached to the foraminous substrate, which runs along the whole circumference of the mat-forming wheel, and (c) a row of through-going mould openings in said flexible material, wherein the mould openings include up-standing walls, and wherein said element is made of a soft material.

5. The mat-forming wheel according to claim 4, wherein the mat-forming wheel includes one said element extending around the whole circumference of the mat-forming wheel.

6. The mat-forming wheel according to claim 4, wherein the mat-forming wheel includes several said elements, each extending over a portion of circumference of the mat-forming wheel.

7. The mat-forming wheel according to claim 4, wherein said element or elements are made of rubber.

8. The mat-forming wheel according to claim 7, wherein said element or elements are made of cellular, neoprene rubber.

9. The mat-forming wheel according to claim 4, wherein said element or elements contains three layers, two layers of soft material and a layer of a stiffening material intermediate these two layers.

10. The mat-forming wheel according to claim 4, wherein the foraminous substrate is a perforated steel plate.

11. The mat-forming wheel according to claim 4, wherein the foraminous substrate is a band of wire mesh.

12. The mat-forming wheel according to claim 4, wherein the soft material is a resilient material allowing compression thereof.

* * * * *